United States Patent [19]
Riza et al.

[11] Patent Number: 5,993,471
[45] Date of Patent: Nov. 30, 1999

[54] TROCAR ASSEMBLY

[75] Inventors: Erol D. Riza, 550 Riverside Dr., Rossford, Ohio 43604; Cosme Ribé Gaya, Woodville, Ohio

[73] Assignee: Erol D. Riza, Rossford, Ohio

[21] Appl. No.: 08/955,735

[22] Filed: Oct. 22, 1997

Related U.S. Application Data

[60] Provisional application No. 60/028,913, Oct. 22, 1996.

[51] Int. Cl.⁶ .................................................. A61B 17/00
[52] U.S. Cl. ............................................................ 606/185
[58] Field of Search ........................... 606/185; 604/164, 604/167, 169, 264

[56] References Cited

U.S. PATENT DOCUMENTS

| | | |
|---|---|---|
| 4,655,752 | 4/1987 | Honkanen et al. . |
| 5,209,736 | 5/1993 | Stephens et al. . |
| 5,211,633 | 5/1993 | Stouder, Jr. . |
| 5,211,634 | 5/1993 | Vaillancourt . |
| 5,300,035 | 4/1994 | Clement . |
| 5,350,364 | 9/1994 | Stephens et al. . |
| 5,354,280 | 10/1994 | Haber et al. . |
| 5,385,552 | 1/1995 | Haber et al. . |
| 5,391,153 | 2/1995 | Haber et al. . |
| 5,391,154 | 2/1995 | Young . |

*Primary Examiner*—Michael Buiz
*Assistant Examiner*—Vikki Trinh
*Attorney, Agent, or Firm*—MacMillan, Sobanski & Todd, LLC

[57] ABSTRACT

A trocar assembly for use in minimally invasive surgery including a housing having an opening formed therethrough and adapted to receive a selected surgical instrument therein. Positioned within the housing is a split seal having a slit extending therethrough. The split seal maintains a seal through the opening of the housing when a surgical instrument is not inserted through the bore of the sleeve. Also positioned within the housing is a seal assembly having a plurality of sealing structures effective to maintain a seal between the housing and a surgical instrument inserted through the bore of the sleeve, such that the plurality of seals accommodate and seal against surgical instruments having different diameters.

24 Claims, 7 Drawing Sheets

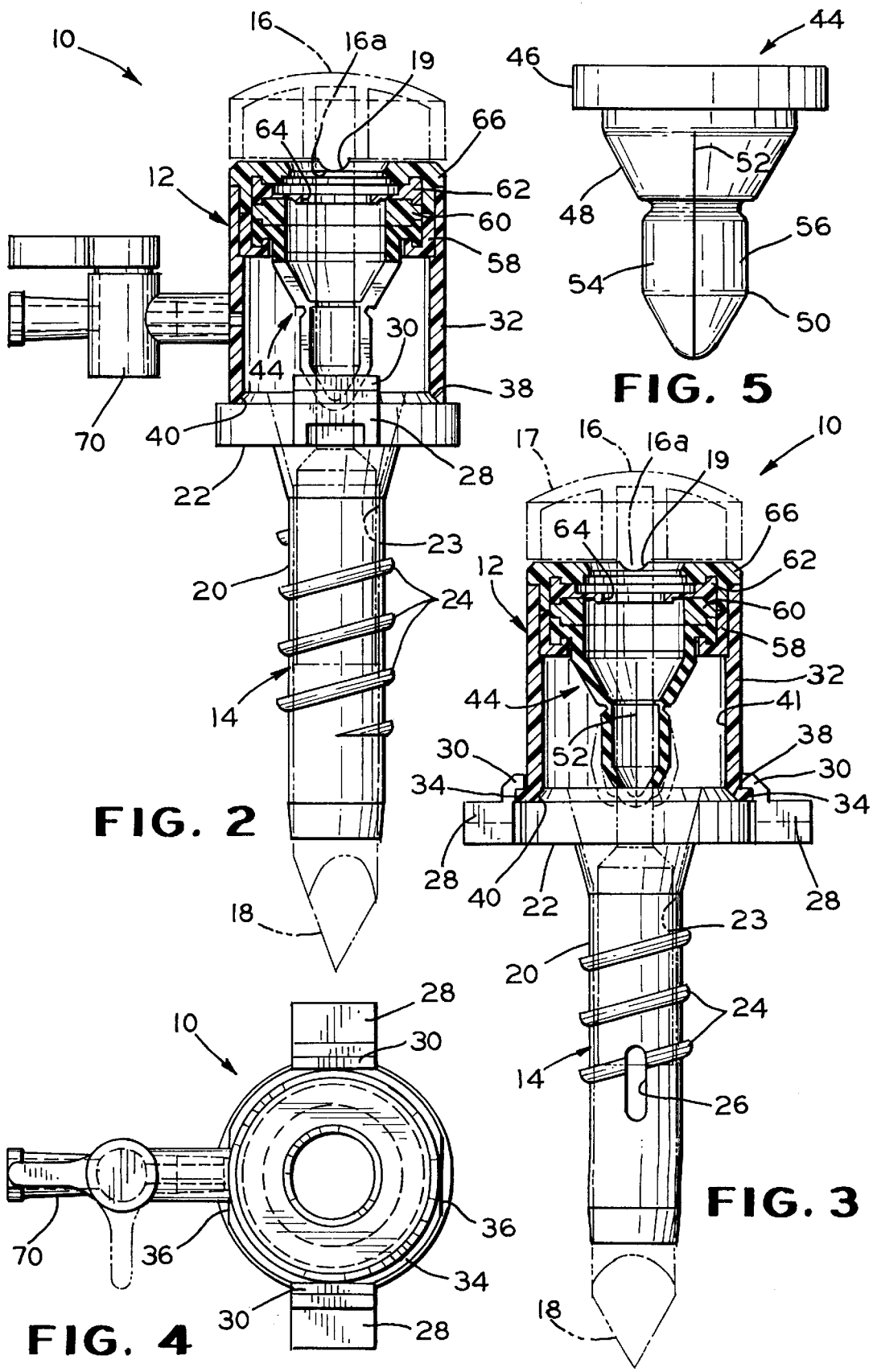

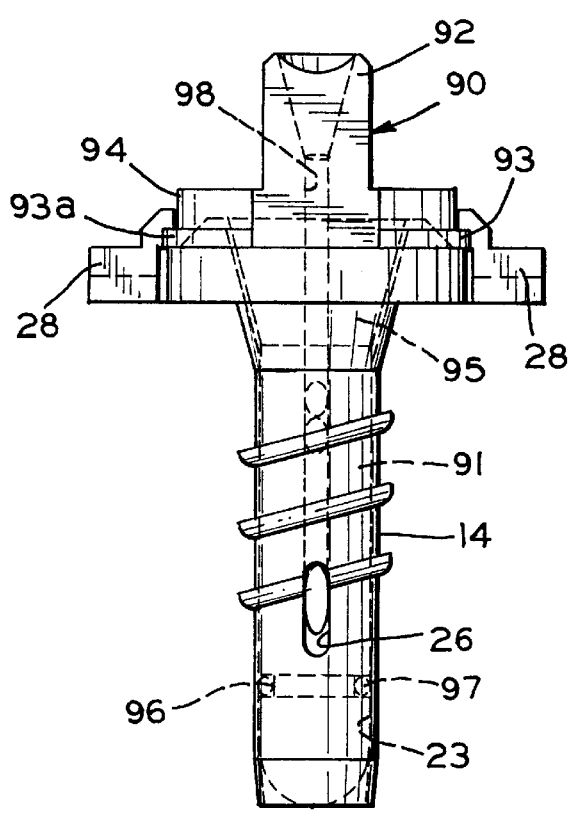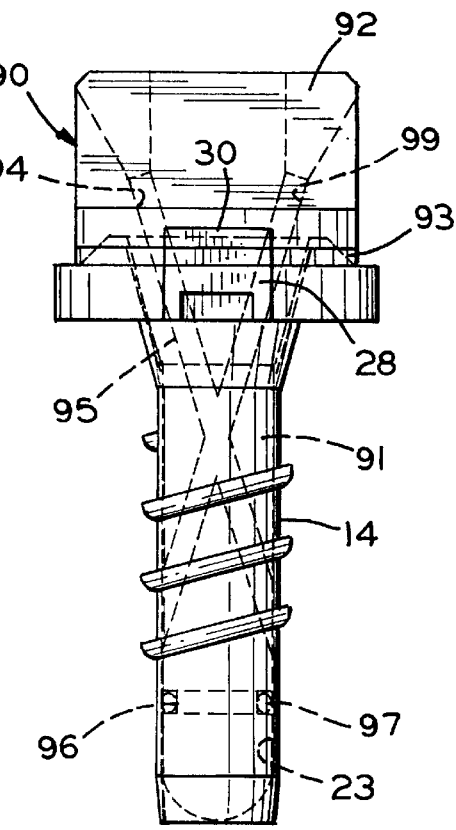
FIG. 8  FIG. 9
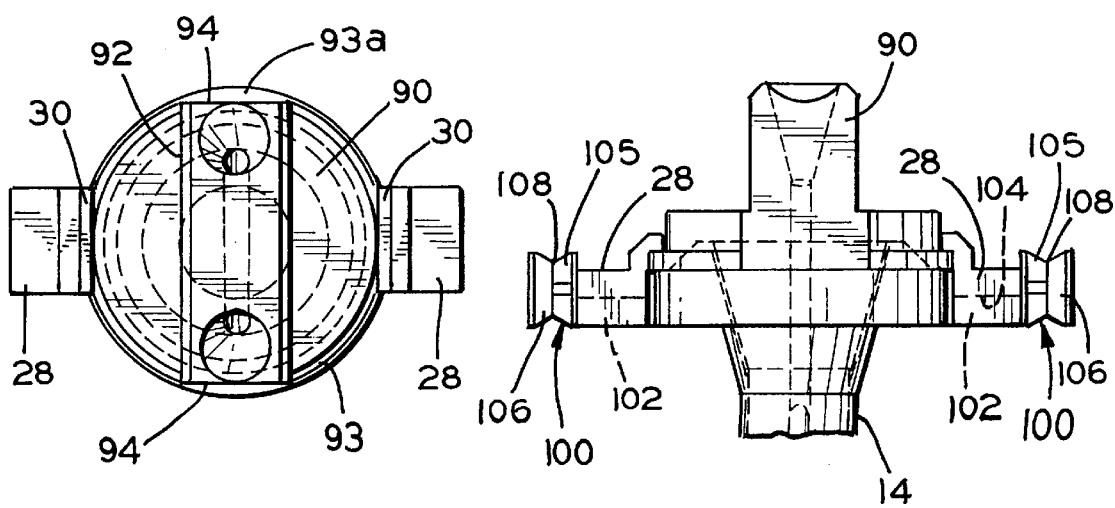
FIG. 10  FIG. 11

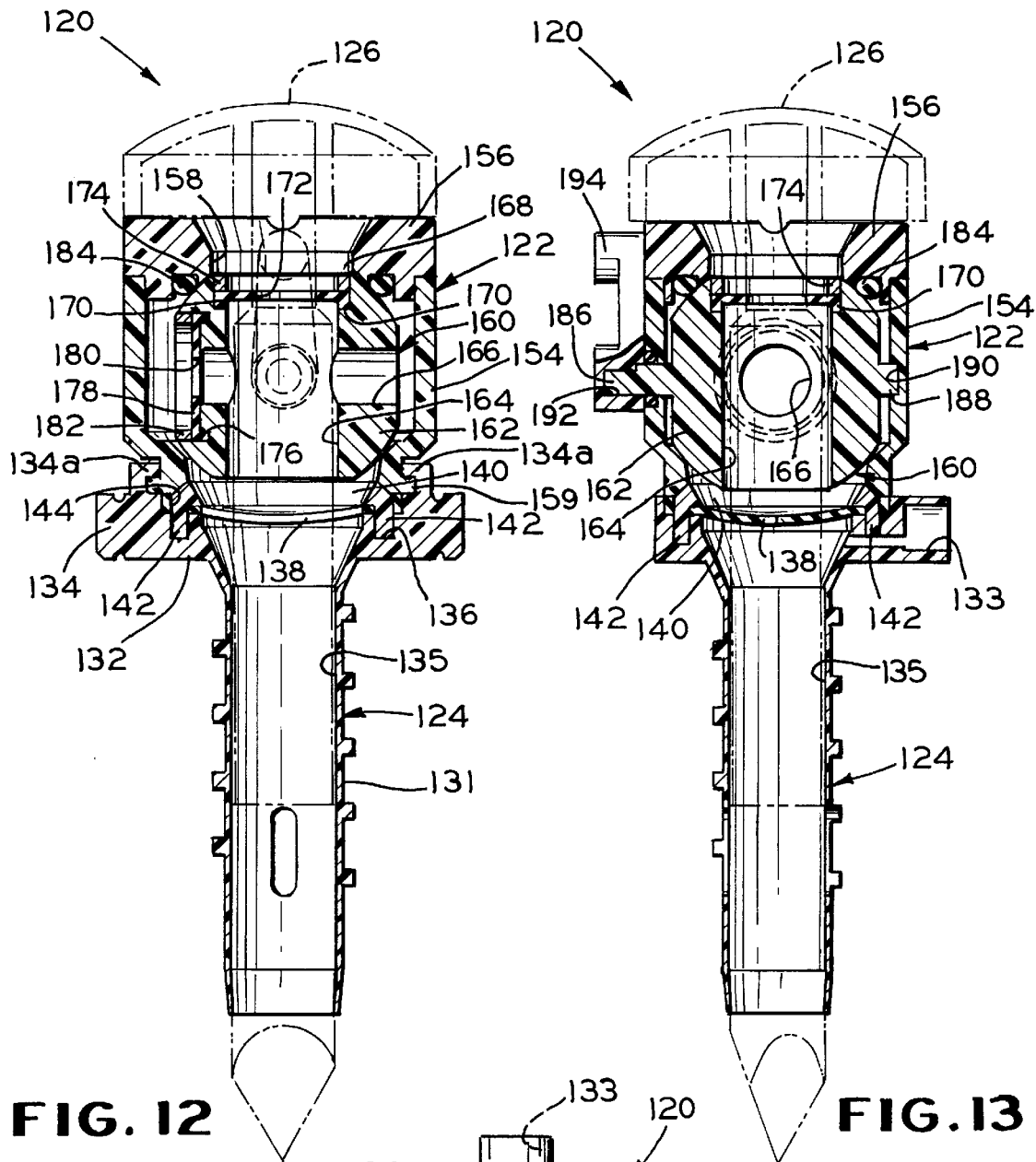
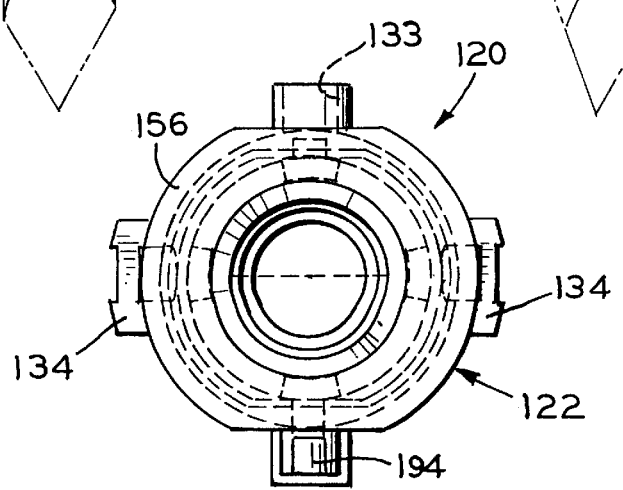
FIG. 12  FIG. 13
FIG. 14

TROCAR ASSEMBLY

CROSS REFERENCE TO RELATED APPLICATIONS

This application claims the benefit of U.S. Provisional Application No. 60/028,913 filed Oct. 22, 1996.

BACKGROUND OF THE INVENTION

This invention relates in general to surgical instruments and in particular to an improved trocar assembly. Trocar assemblies are used in laparoscopic and other minimally invasive surgical procedures to puncture the abdominal wall and to form an opening or conduit therethrough. A physician can then perform the surgery through the relatively small opening which is held open by the trocar assembly. An inert gas is typically introduced into the abdominal cavity to expand the abdominal cavity. Surgical instruments or optical devices can then be inserted through a longitudinal bore formed through the trocar assembly for access to the expanded abdomen cavity.

Trocar assemblies typically include seals which generally prevent the inert gas from escaping from the abdominal cavity. The seals also permit the insertion of a shaft of an optical device or surgical instrument through the longitudinal bore of the trocar assembly while generally maintaining a seal during the insertion of the surgical instrument. Some trocar assemblies include multiple seals to allow for the sealing of surgical instruments having different shaft diameters which may be used throughout the operation. Typical shaft diameters are 5 mm, 10 mm, and 12 mm. To change to the desired sized seal, the surgeon is generally required to manipulate the trocar assembly in some manner so as to change the position of the seals until the desired sized seal is aligned with the longitudinal bore formed through the trocar assembly. For many of the trocar assemblies having multiple seals, it is often cumbersome for the surgeon to manipulate the trocar assembly to position the desired sized seal. These types of trocar assemblies typically require the use of both hands of the surgeon, which is generally undesirable. It is therefore desirable to have a trocar assembly which is easy to use and provides for sealing of inert gas from within the abdominal cavity while allowing for different surgical instrument shaft diameters to be inserted therethrough.

BRIEF SUMMARY OF THE INVENTION

This invention relates in general to an improved trocar assembly for use in minimally invasive surgery. The trocar assembly includes a housing having an opening formed therethrough. A sleeve, fastened to the housing, is adapted to be inserted into a puncture wound through an abdominal wall of a patient for the passage of surgical instruments through the bore of the sleeve. The sleeve can be a separate structure removably fastened to the housing, or an integral part of the housing. Positioned within the housing is a split seal having a slit extending therethrough. The split seal maintains a seal through the bore of the sleeve when a surgical instrument is not inserted through the bore of -the housing. Also positioned within the housing is a seal assembly having a plurality of sealing structures effective to maintain a seal between the housing and a surgical instrument inserted through the opening of the housing, such that the plurality of seals accommodate surgical instruments having different diameters.

In one specific embodiment of the invention, the seal assembly includes first and second seals, the combination of which maintain a seal between the housing and a surgical instrument inserted through the opening of the housing. The first seal is adapted to maintain a seal between the housing and a surgical instrument having a first diameter. The second seal is adapted to maintain a seal between the housing and a surgical instrument having a second diameter, wherein the first and second diameters are different. The split seal and the second seal can be formed from a single elastomeric seal structure, wherein the second seal is a radially inwardly extending circumferential annular bead formed on a pair of lips defined by the slit of the split seal.

In another specific embodiment of the invention, the seal assembly includes a ball rotatably mounted within the housing and movable to first and second operating positions. The ball has first and second bores extending through the ball. The first bore is in axial alignment with the opening of the housing when the ball is in the first operating position. The second bore is in axial alignment with the opening of the housing when the ball is in the second operating position. A first seal is positioned within the first bore of the ball and is adapted to maintain a seal between the housing and a surgical instrument having a first diameter which is inserted through the first bore of the ball. A second seal is positioned within the second bore of the ball and is adapted to maintain a seal between the housing and a surgical instrument having a second diameter, different from the first diameter, which is inserted through the second bore of the ball.

Various objects and advantages of this invention will become apparent to those skilled in the art from the following detailed description of the preferred embodiment, when read in light of the accompanying drawings.

BRIEF DESCRIPTION OF THE SEVERAL VIEWS OF THE DRAWING

FIG. 2 is a sectional view of the trocar assembly illustrated in FIG. 1.

FIG. 3 is a sectional view of the trocar assembly taken along lines 3—3 of FIG. 1.

FIG. 4 is top plan view of the trocar assembly illustrated in FIG. 1.

FIG. 5 is a side elevational view of the split seal of the trocar assembly lllustrated in FIG. 1.

FIG. 8 is a front elevational view of a plug used in cooperation with the sleeve of the trocar assembly illustrated in FIG. 1.

FIG. 9 is a side elevational view of the plug and sleeve illustrated in FIG. 8.

FIG. 10 is a top plan view of the plug and sleeve illustrated in FIG. 8.

FIG. 11 is a second embodiment of a sleeve having suture tie down structures.

FIG. 12 is a front sectional view of a second embodiment of a trocar assembly, in accordance with the present invention.

FIG. 13 is a side sectional view of the trocar assembly illustrated in FIG. 12.

FIG. 14 is a elevational top plan view of the trocar assembly illustrated in FIG. 12.

DETAILED DESCRIPTION OF THE INVENTION

Figure 1:
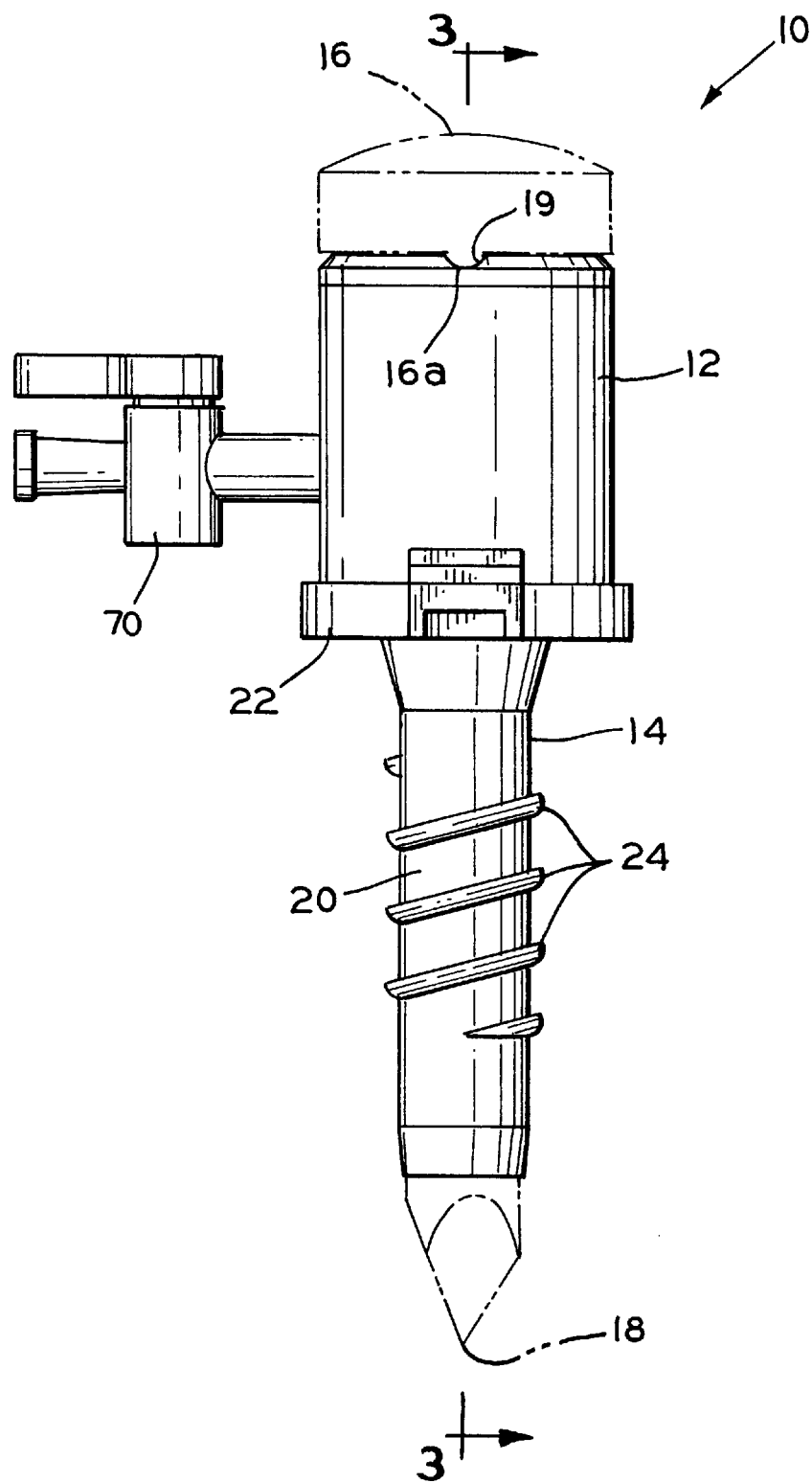
FIG. 1 is an elevational view of a first embodiment of a trocar assembly, in accordance with the present invention.

In the following description of the invention, certain terminology will be used for the purpose of reference only, and are not intended to be limiting. Terms such as "upper", "lower", "above", "below", "rightward", "leftward", "clockwise", and "counterclockwise" refer to directions in the drawings to which reference is made. Terms such as "inward" and "outward" refer to directions toward and away from, respectively, the geometric center of the component described. Terms such as "front", "rear", "side", "leftside", "rightside", "top", "bottom", "horizontal", and "vertical" describe the orientation of portions of the component within a consistent but arbitrary frame of reference which is made clear by reference to the text and the associated drawings describing the component under discussion. Such terminology will include the words specifically mentioned above, derivatives thereof, and words of similar import.

As used in this application and the claims thereof, the term 'removably fastened', as applied to one component being attached to another component, means that the two components are joined in a manner designed to allow the two components to be subsequently unfastened from each other in a non-destructive manner, that is, without permanently deforming or damaging either of the two components.

Referring now to the drawings, there is illustrated in FIGS. 1 through 4 a first embodiment of a trocar assembly, indicated generally at 10, in accordance with the present invention. As used in this application, "proximal" means that portion of the structure under discussion which is normally close to the user when the trocar assembly 10 is in use. Similarly, "distal" refers to that portion of the structure under discussion which is farther away from the user holding the trocar assembly 10. The trocar assembly 10 includes a generally cylindrical hollow housing 12 and a tubular distal sleeve 14 removably attached to the distal end of the housing 12. A stylet 16, shown in phantom, can be used with the trocar assembly 10. The stylet 16 is axially disposed within the housing 12 and the sleeve 14. The stylet 16 is used for initial insertion of the trocar assembly 10 through an abdominal wall of a patient and can be later removed from the housing 12 and the sleeve 14. The stylet 16 has a sharp distal end 18 for assisting in puncturing and inserting the trocar assembly 10 through the abdominal wall. An obturator (not shown), having a distal blunt end which helps prevent accidental puncturing of internal organs, may be suitably used with the trocar assembly 10 instead of the sharp pointed stylet 16 if desired. The stylet 16 has an enlarged proximal head 17 preferably having a plurality of radially extending ribs 16a on a distal side thereof which mate with corresponding radial grooves 19 formed on the proximal end surface the housing 12, as shown in FIGS. 1 through 3. The ribs 16a and the grooves 19 cooperate to prevent rotation of the stylet 16 with respect to the housing 12 during insertion of the trocar assembly through the abdominal wall.

The sleeve 14 includes a distal tubular portion 20 and a circumferential flange 22 extending radially outwardly from a proximal end of the tubular portion 20. A through-bore 23 extends axially through the sleeve 14. Preferably, the tubular portion 20 has external helical threads 24 formed on the outer surface thereof for assisting in the insertion, removal, and retention of the sleeve 14 within the opening of the abdominal wall. The threads 24 may be replaced by circumferentially extending axially spaced ribs or flanges (not shown) if desired. Alternatively the threads 24 may be omitted entirely and the sleeve 14 can be used in cooperation with a separate gripper (not shown), such as that shown in my U.S. Pat. No. 5,562,688, the disclosure of which is incorporated herein by reference.

The tubular portion 20 of the sleeve 14 has a pair of opposed longitudinal slots 26 formed therethrough, the purpose of which will be explained below. The flange 22 includes a pair of opposed tabs 28 extending radially outwardly therefrom. A finger portion 30 extends radially inwardly from the proximal surface of each tab 28. An external frustoconical surface 38 extends outwardly and distally from the proximal end of the flange 22. The finger portions 30 and the frustoconical surface 38 assist in removably fastening the housing 12 to the sleeve 14, as will be described in detail below.

The housing 12 includes a generally cylindrical outer shell 32 having a flange 34 extending radially outwardly therefrom. Positioned internally from the flange 34 is a frustoconical surface 40 formed on an internal wall 41 of the outer shell 32. As best seen in FIG. 4, the flange 34 has a pair of opposing flats 36 formed in the flange 34. The flats 36 provide for a means for removably fastening the housing 12 to the sleeve 14, as will be discussed below.

Figure 6:
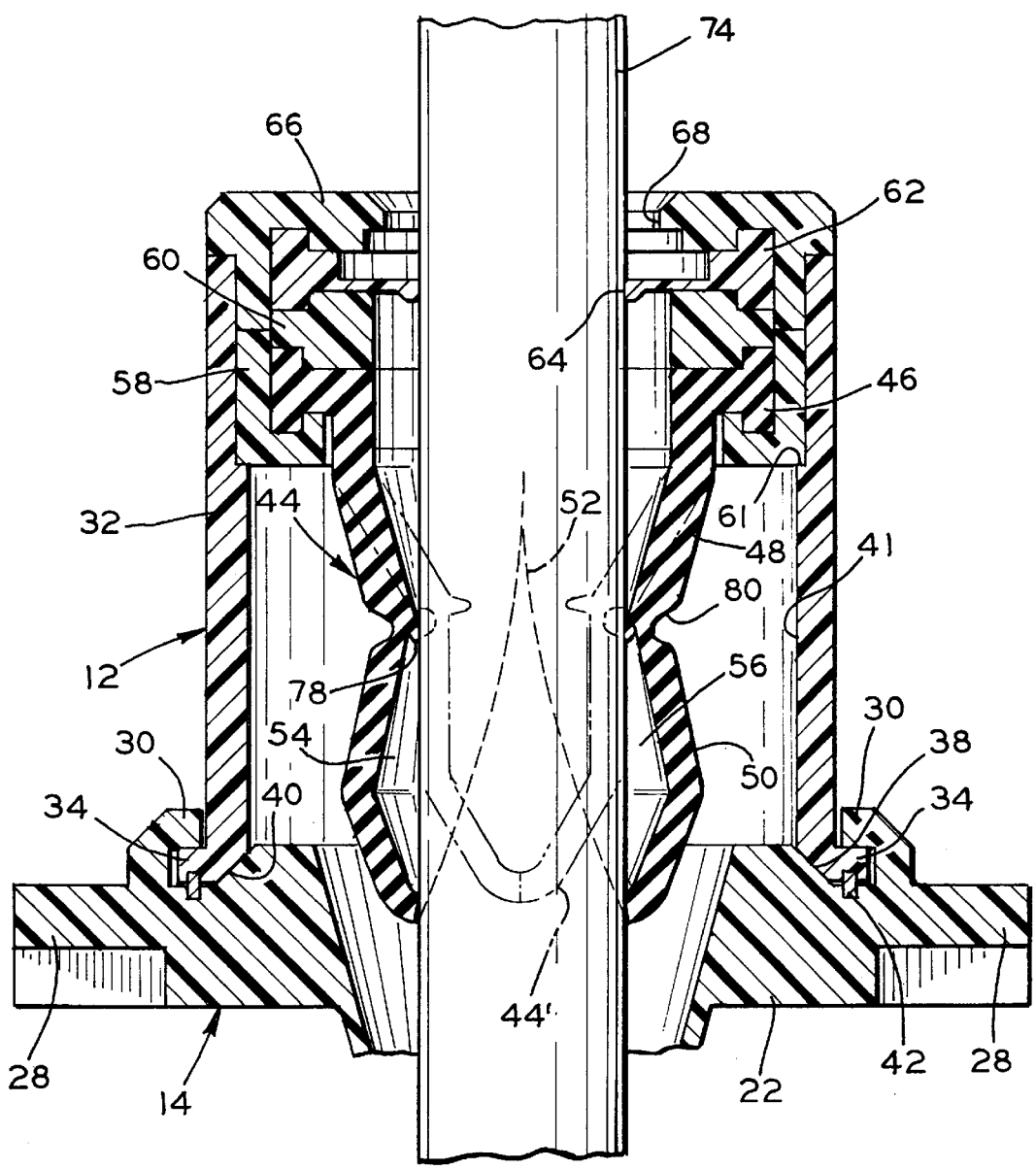
FIG. 6 is an enlarged sectional view of a portion of the trocar assembly illustrated in FIG. 1, wherein a relatively large diameter shaft of a surgical instrument is inserted through the trocar assembly.
Figure 7:
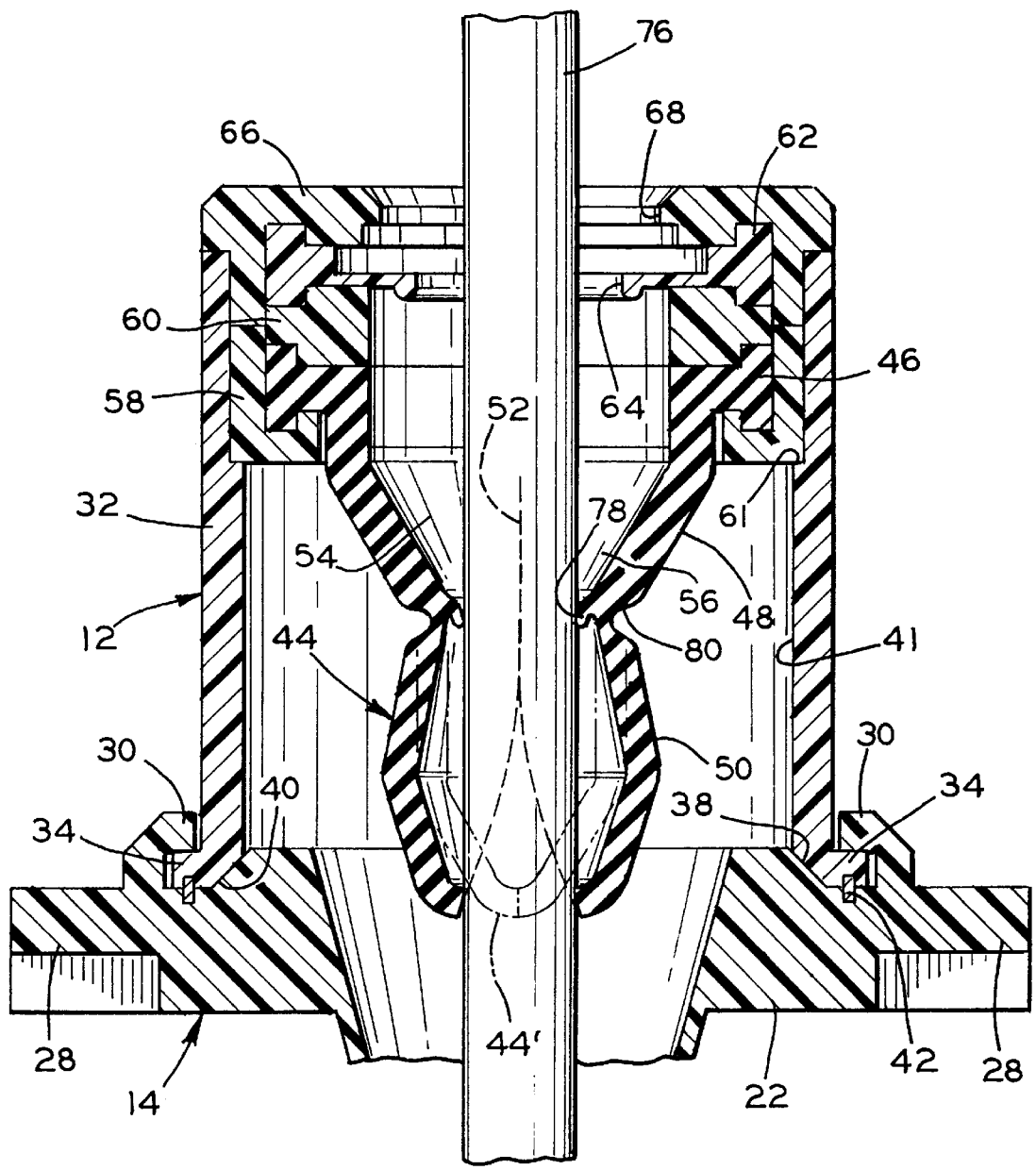
FIG. 7 is an enlarged sectional view of a portion of the trocar assembly illustrated in FIG. 1, wherein a relatively small diameter shaft of a surgical instrument is inserted through the trocar assembly.
Figure 15:
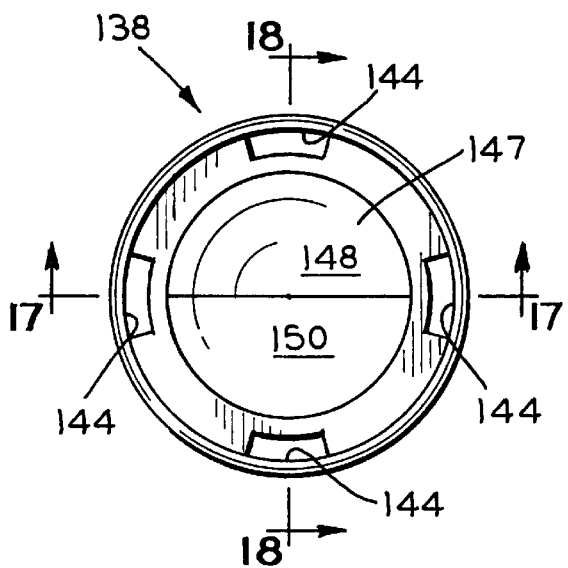
FIG. 15 is an elevational top plan view of a flap seal of the trocar assembly illustrated in FIG. 12.
Figure 16:
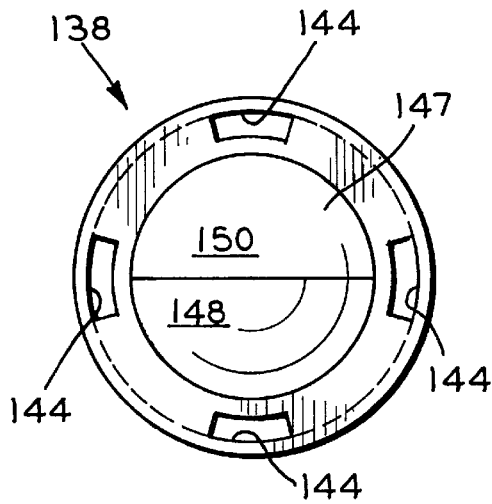
FIG. 16 is a bottom plan view of the flap seal illustrated in FIG. 15.

The trocar assembly 10 further includes an annular shaped split seal 44. As best shown in FIGS. 5 through 7, the split seal 44 includes a proximal annular flange 46, a frustoconical intermediate portion 48, and a distal tip portion 50. The split seal 44 has a slit 52 extending laterally through the intermediate portion 48 and the distal tip portion 50, thereby forming a pair of adjacent inwardly and distally extending seal lips 54 and 56.

The split seal 44 is retained within the housing 12 by an annular retainer ring 58 and an annular spacer 60. The retainer ring 58 is seated on a circumferential ledge 61 which is formed on the inner wall 41 of the outer shell 32. The flange 46 of the split seal 44 is positioned between the retainer ring 58 and the spacer 60. An annular seal 62 having an axial opening 64 is positioned above the spacer 60. An annular cap 66 having an opening 68 is attached to the outer shell 32. The opening 68 and the hollow outer shell 32 defame an opening formed through the housing 12 which is axially aligned with the bore 23 formed through the sleeve 14. The cap 66 can be fastened to the outer shell 32 by any suitable means, such as by an adhesive. Although the cap 66 is illustrated and described as a separate structure, the cap 66 can be integral with the outer shell 32 of the housing 12. The retainer ring 58 cooperates with the cap 66 to retain the annular seal 62, the spacer 60, and the split seal 44. Of course, the split seal 44 can be retained in the housing 12 by any suitable means. Attached to the outer shell 32 is a conventional stopcock 70 in communication with a through hole 72 formed through the outer shell 32.

As best shown in FIGS. 6 and 7, the split seal 44 further includes an internal annular bead 78 located near the narrow end of the frustoconical portion 48 of the split seal 44. The split seal 44 also has an outer circumferential groove 80 between the conical section 48 and the lower tip portion 50, the reason for which will be explained in detail below.

To fasten the housing 12 to the sleeve 14, the flats 36 of the flange 34 are rotationally aligned with the tabs 28 of the sleeve 14. The housing 12 is then moved distally until the frustoconical surface 40 formed on the flange 34 of the housing 12 contacts the frustoconical surface 38 formed on the flange 22 of the sleeve 14. The outer shell 32 is then rotationally turned approximately 90 degrees with respect to the sleeve 14 so that the finger portions 30 of the tabs 28 extend over the flange 34 of the outer shell 32, thus fastening the housing 12 to the sleeve 14 by a frictional fit. Of course, the housing 12 can be removably fastened to the sleeve 14 by any suitable means. For additional sealing between the housing 12 and the sleeve 14, an annular seal 42 can be positioned between the flange 22 of the sleeve 14 and the flange 34 of the outer shell 32, as shown in FIGS. 6 and 7.

The housing 12 of the trocar assembly 10 functions to maintain a generally air and fluid tight seal between the interior of the housing 12 and an outer surface of a surgical instrument inserted therethrough. The seal is generally maintained even though such surgical instruments have various sized diameters. Surgical instruments used in laparoscopic surgical procedures commonly have different shaft diameters. Nominal shaft diameters of 5 mm, 10 mm, and 12 mm are typical of the surgical instruments used at the present.

During laparoscopic and other minimally invasive surgical procedures, the sleeve 14 of the trocar assembly 10 is inserted into a puncture formed through the abdominal wall of the patient. Typically an inert gas is introduced into the abdominal cavity to expand the abdomen. The split seal 44 helps to prevent the inert gas from escaping through the trocar assembly 10. To introduce the inert gas, the stopcock 70 is first connected to an inert gas pressure source (not shown) to control the gas flow. The stop cock 70 is then opened to allow gas to enter the housing 12. The gas passes through the bore 23 of the sleeve 14, and into the abdominal cavity, thereby expanding the abdominal cavity. The pressure of the gas itself assists in urging seal lips 54 and 56 into sealing engagement with each other, thereby preventing the gas to escape.

The trocar assembly 10 enables the physician to insert surgical instruments or optical devices through the trocar assembly 10. Referring FIG. 6, a relatively large diameter surgical instrument shaft 74, such as an instrument having a shaft diameter of 10 or 12 mm, is shown extending through the trocar assembly 10. The shaft 74 extends through the housing 12 and the split seal 44, causing the seal lips 54 and 56 to spread apart from one another. Note that the split seal 44 is shown in phantom lines 44' to represent the position of the seal lips 54 and 50 when no surgical instrument is inserted therethrough. The pressurized gas within the abdominal cavity is generally prevented from escaping through the opening 68 of the cap 66 by the sealing engagement of the annular seal 62 on the outer surface of the shaft 74. Preferably, the annular seal 62 is made of an elastomeric material having low frictional drag characteristics which can be deflected relatively easily to accommodate slightly different diameter shafts, for example, 10 mm and 12 mm diameter shafts.

FIG. 7 illustrates a surgical instrument shaft 76 having a smaller diameter shaft 76 compared to the shaft 74 of FIG. 6. For example, the surgical instrument shaft could be 5 mm in diameter which is a typical shaft diameter for a surgical instrument. The diameter of the shaft 76 is smaller than the diameter of the opening 64 of the annular seal 62, and therefore no sealing engagement occurs between the annular seal 62 and the shaft 76. However, the shaft 76 and the annular bead 78 of the split seal 44 cooperate to provide for a sealing arrangement. Preferably, the annular bead 78 has an internal diameter slightly smaller than the outer diameter of the shaft 76. Preferably, the wall thickness of the split seal 44 adjacent the outer groove 80 is relatively thin. When the shaft 76 is inserted through the housing 12, the seal lips 54 and 56 of the split seal 44 deflect at the thin walled portion adjacent the outer groove 80, thereby causing only the lower tip portions 50 of the seal lips 54 and 56 to deflect and not the frustoconical portions 48 of the seal lips 54 and 56. Thus, the internal bead 78 of the split seal 44 does not significantly deflect, and retains a circumferential sealing engagement with the outer surface of the shaft 76.

Due to the unique design of the trocar assembly 10, the trocar assembly 10 does not have to be manually adjusted by the surgeon during surgery when using various surgical instruments each having a different diameter. In many prior art trocar assemblies, the surgeon must manipulate the trocar assembly in some way using two hands, such as changing housings or sliding various sealing structures into different positions every time a surgical instrument having a different diameter is used. For the trocar assembly 10, the surgeon simply removes one surgical instrument and inserts another, during which process a generally air tight seal is maintained.

Preferably the contact surface area between the bead 78 of the split seal 44 and the surgical instrument is relatively small so that a low frictional drag force acts on the surgical instrument when inserting and removing the surgical instrument. This provides for easy manipulation of the surgical instrument by the surgeon. Likewise, the contact surface area between the annular seal 62 and a larger diameter surgical instrument is also preferably relatively small such that only low drag forces are generated when inserting and removing the surgical instrument.

The trocar assembly 10 of the present invention may also include a plug 90, as shown in FIGS. 8 through 10, removably installed in the sleeve 14 of the trocar assembly 10 in place of the housing 12. The plug 90 is provided to assist in the suturing the surgical opening or puncture wound in the abdominal wall. The plug 90 has a generally cylindrical body 91 and an enlarged proximal end 92. Preferably, the proximal end 92 has a laterally extending cylindrical flange 93. As best seen in FIG. 10, the flange 93 has a pair of opposing flats 94 formed in the flange 93. The flats 94 provide for a means for connecting the plug 90 to the sleeve 14, similar to the connection between the housing 12 and the sleeve 14, as described above with respect to connection of the housing 12 to the sleeve 14. The body 91 and the enlarged proximal end 92 of the plug 90 are joined together by an intermediate frustoconical portion 95. The body 91 has a circumferential groove 96 formed about the distal end thereof which retains a sealing member, such as an O-ring 97. The O-ring 97 provides for a relatively air and fluid tight seal between the external surface of the plug 90 and the wall of the bore 23 of the sleeve 14. The plug 90 further includes two intersecting diagonal passageways 98 and 99 which extend through the enlarged proximal end 92 and a portion of the body 91. If desired, the plug 90 can be provided with a stop (not shown) to halt rotation when assembling the plug 90 into the sleeve 14 at the point where the passageways 98 and 99 of the plug 90 and the slots 26 of the sleeve 14 are aligned. Alternatively or additionally, the plug 90 can be provided with visual indicia (not shown) to provide manual alignment of the passageways 98 and 99 and the slots 26. The passageways 98 and 99 are provided for the acceptance of a surgical instrument for suturing of the opening in the abdominal wall. The alignment of the openings of the passageways 98 and 99 of the plug 90 and the slots 26 of the sleeve 14 allow for passage of a surgical instrument from the proximal end of the plug 90, external to the abdominal wall, through the slots 26 to a selected point in the abdominal wall. The trocar assembly 10 may be positioned, for example, with the slots 26 of the sleeve 14 positioned just outwardly of the muscle layer in the abdominal wall. Thus, a suturing instrument (not shown) can be used in cooperation with the plug 90 and the sleeve 14 to position a suture adjacent the muscle layer.

FIG. 11 shows an alternate embodiment of the trocar assembly 10 in which the sleeve 14 has tie-down fixtures 100 mourned on the pair of tabs 28. The tie-down fixtures 100 extend radially outwardly from the tabs 28. The tie-down fixtures 100 provide a means for securing or anchoring the sleeve 14 to the abdominal wall by respective sutures. Suturing the sleeve to the abdominal wall in this fashion helps prevent the sleeve 14 from sliding out of the surgical opening in the abdominal wall. Each tie-down fixture 100 has a stem 102 which extends into a slot 104 formed in the tabs 28 of the sleeve 14. The tie-down fixtures 100 can be attached to the tabs 28 by any suitable means, such as by adhesive or by a suitable "snap-on" arrangement between cooperating structures formed on the tabs 28 and the tie-down fixtures 100. Each tie-down fixture 100 has a pair of annular shaped buttons 105 and 106 which are spaced apart from one another, thereby creating a slight gap 108 therebetween. Preferably, the gap 108 is slightly smaller than the width of a suture (not shown) so that a suture inserted or wound several times into the gap is frictionally held in place. In order to secure the trocar assembly 10 in place within a surgical opening or puncture wound in a patient's abdominal wall, the surgeon inserts a stitch with a suture (not shown) through the skin adjacent the opening in the abdominal wall. The suture is then wound around the adjacent tie-down fixture 100, between the buttons 105 and 106 thereof, to secure one side of the sleeve of the trocar assembly 10. Repeating this procedure on the other side of the sleeve 14 securely anchors the sleeve 14 to the abdominal wall.

It is contemplated that the trocar assembly 10 can further include a second split seal (not shown) which is similar in structure to the split seal 44 but being slightly larger. The second split seal can be placed around the split seal 44 and positioned such that the longitudinal slit extending through the second seal defines a plane which is perpendicular to the plane defamed by the slit 52 of the split seal 44. Thus, the split seal 44 and the second split seal would cooperate to provide an enhanced sealing structure for a shaft of a surgical instrument inserted through both of the split seals.

Although the trocar assembly 10 was illustrated and described as having a separate housing 12 with a selectively connectable sleeve 14, it is anticipated that the sleeve 14 can be formed as a non-detachable, integral part of the housing 12.

FIGS. 12 through 14 illustrate a second embodiment of a trocar assembly, indicated generally at 120. The trocar assembly 120 generally includes a cylindrical housing 122 and a tubular sleeve 124 which is similar in fiction and structure to the sleeve 14 of the trocar assembly 10. A stylet, shown in phantom lines 126 in FIGS. 12 and 13, is positioned within the housing 1-22 and the sleeve 124. The stylet 126 is similar in function and construction as the stylet 16 shown in FIGS. 1 through 3.

The sleeve 124 includes a distal tubular portion 131 and circumferential flange 132 extending radially outwardly from the proximal end of the sleeve 124. As best seen in FIG. 13, the flange 132 of the sleeve 124 has a conduit 133 formed therethrough, which can be connected to a source of pressurized inert gas (not shown) to permit inert gas to flow into the abdominal cavity of a patient. A stopcock (not shown) may also be attached between the conduit 152 and the source of pressurized gas. The sleeve 124 includes a pair of opposed tabs 134 extending radially outwardly therefrom. A finger portion 134a extends radially inwardly from the proximal surface of each tab 134. The sleeve 124 has an axially extending bore 135 therethrough, through which the stylet 126 is inserted. The flange 132 of the sleeve 124 has a multi-stepped annular groove 136 formed in the proximal end thereof The trocar assembly 120 further includes an annular shaped split or flap seal 138 and a retainer ring 140 which retains the flap seal 138 in the proximal end of the sleeve 124. The retainer ring 140 is formed with a plurality of axially extending circumferentially spaced tabs 142 which entered into the annular groove 136 formed in the sleeve 124.

Figure 17:
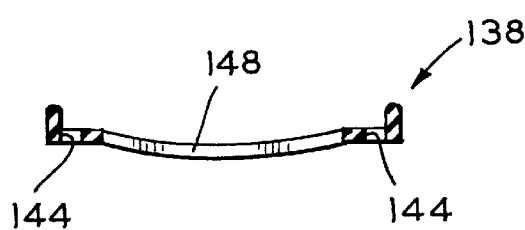
FIG. 17 is a sectional view of the flap seal taken along lines 17—17 of FIG. 15.
Figure 18:
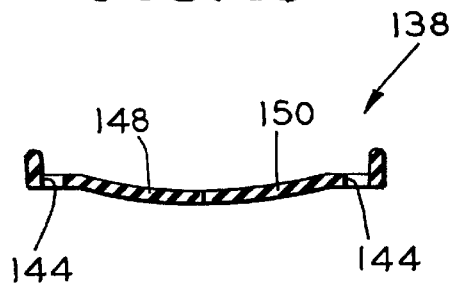
FIG. 18 is a sectional view of the flap seal taken along lines 18—18 of FIG. 15.

The flap seal 138 is shown in detail in FIGS. 15 through 18. Generally, the flap seal 138 functions in a similar manner as the distal portions of the seal lips 54 and 56 of the split seal 44 to help prevent the insufflation gas from escaping from the abdominal cavity out through the trocar assembly 120 when there is no surgical instrument present in the trocar assembly 120. The flap seal 138 is a cup-shaped diaphragm which extends across the bore 135 of the sleeve 124 to seal the bore 135 when no surgical instrument is inserted therethrough. The flap seal 138 has a plurality of openings 144 formed generally about the perimeter thereof which accept the plurality of tabs 142 of the retainer ring 140 to retain the flap seal 138 in the sleeve 124. The flap seal 138 has a slit 146 extending laterally across a central portion 147 of the flap seal 138. The central portion 147 is convex shaped in the distal direction, as best shown in FIGS. 17 and 18. Two generally semi-circular inwardly and distally extending flaps 148 and 150 are defamed by the central portion 147 and the slit 146. The flap seal 138 is preferably formed of an elastomeric substance whose resilient nature will normally urge the flaps 148 and 150 into sealing engagement with one another. The convex shaped structure of the central portion 147 of the flap seal 138 is such that the pressure insufflation gas trying to escape from the abdominal cavity will aid in holding the flaps 148 and 150 in sealing engagement. More specifically, pressurized insufflation gas from the abdominal cavity will urge the convex shaped flaps 148 and 150 into sealing engagement with each other, thereby forcefully holding the slit 146 closed. When a surgical instrument is inserted into the trocar assembly 120, the flaps 148 and 150 will simply deflect distally, thereby permitting passage of the surgical instrument through the slit 146.

Referring to FIGS. 12 through 14, the housing 122 includes a generally cylindrical outer shell 154 and a cap 156 attached to the proximal end of the outer shell 154. The cap 156 can be attached to the housing 122 by any suitable methods, such as by an adhesive. The cap 156 has a central axially extending opening 158 through which a surgical instrument can be inserted. The housing 122 includes a circumferential flange 159 extending radially outwardly from the distal end thereof. The sleeve 124 is removably fastened to the housing 122 in generally the same manner as the sleeve 14 and the housing 12 of the trocar assembly 10, with the finger portions 134a of the sleeve 124 releasably engaging the flange 159 of the housing 122.

Figure 19:
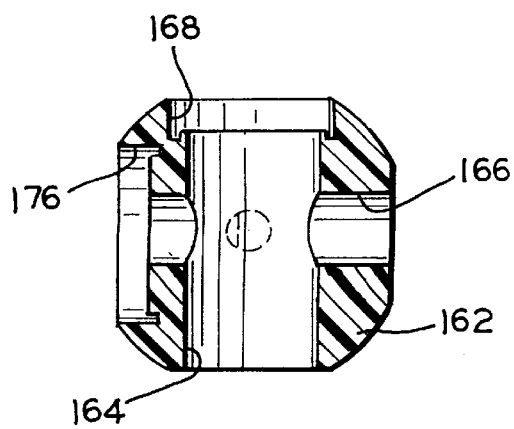
FIG. 19 is a section view of a ball of the trocar assembly illustrated in FIG. 12.

The housing 122 further includes a two-position ball housing, indicated generally at 160 which provides for sealing when surgical instruments are is inserted through the trocar assembly 120. The ball housing 160 includes a rotatably mounted generally spherical shaped ball 162. As best seen in FIG. 19, the ball 162 has two bores 164 and 166 formed therethrough which intersect generally at the center of the ball 162. The bores 164 and 166 are generally positioned at right angles to one another. An annular recess 176 is formed in the ball 162 located adjacent the opening of one end of the bore 164. An annular recess 176 is formed in the ball 162 located adjacent the opening of one end of the bore 166. As shown in FIGS. 12 and 13, the ball housing 160 further includes an annular seal 170 seated within the recess 168 of the ball 162. The annular seal 160 has a central opening 172 formed therethrough. The seal 170 is retained in the recess 168 of the ball 162 by an annular retainer 174. An annular seal 178 having a central opening 180 is positioned within the recess 176 of the ball 162. The seal 178 is retained in the recess 176 by an annular retainer 182. The ball housing 160 further includes an O-ring seal 184 sealingly engaging both the outer surface of the ball 162 and the cap 156.

The ball 162 is rotatably mounted in the housing 122 on two opposed arms 186 and 188 (FIG. 13). The arms 186 and 188 extend outwardly along the axis of rotation of the ball 162. The arm 188 extends into a recess 190 formed in the outer shell 154 of the housing 122. The arm 186 extends through a hole 192 formed through the outer shell 154 of the ball housing 160. A lever arm 194, shown partially in section in FIG. 13, is attached to the end of the arm 186. The ball 162 can be operatively moved to two operating positions by manually rotating the lever arm 194 through a 90 degree arc. The two operating positions of the ball 162 correspond respectively a first position in which the bore 164 is aligned with the longitudinal axis of the sleeve 124 and a second position in which the bore 166 is aligned with the longitudinal axis of the sleeve 124.

The two positions of the ball 162 permit sealing for surgical instruments having various sized shaft diameters. The opening 180 of the annular seal 178 is smaller than the opening 172 of the annular seal 170. The opening 180 of the annular seal 178 is preferably dimensioned so as to provide for sealing engagement with relatively small diameter surgical instruments, such as for example, a 5 mm diameter surgical instrument shaft. The opening 172 of the circular seal 170 is preferably dimensioned so as to provide sealing engagement with relatively large diameter surgical instruments, such as for example, a 10 or 12 mm diameter surgical instrument shaft.

For operation of the trocar assembly 120, the surgeon rotates the lever arm 194 to one of the two positions which correspond to the appropriately sized annular seal 170 or 178 for the selected surgical instrument. For example, as shown in FIGS. 12 and 13, the ball 162 is in the first position such that the bore 164 is aligned for a surgical instrument having a relatively large shaft diameter, such as 10 or 12 mm. The sealing engagement between the surgical instrument and the annular seal 170 limits pressurized gas from escaping from the abdominal cavity through the trocar assembly 120 while permitting an access port for the surgical instrument into the abdominal cavity. When the surgical instrument is removed, the flap seal 138 closes to provide a generally air-tight seal through the trocar assembly 120. If the surgeon desires to use a smaller surgical instrument, the surgeon simply rotates the lever arm 194 approximately 90 degrees to move the ball 162 to the second position such that the bore 166 is aligned with the longitudinal axis of the sleeve 124. The surgeon then simply inserts the surgical instrument through the trocar assembly 120 and the annular seal 178 will provide sealing between the surgical instrument and the trocar assembly 120.

The trocar assembly 120 can also be used with a plug (not shown) similar to the plug 90 of the trocar assembly 10.

An advantage of the trocar assembly 120 over prior art trocar assemblies is the ease of adjustment for different diameter sized surgical instruments. The trocar assembly 120 can easily be adjusted by one hand. For example, the surgeon can hold the trocar assembly 120 in the palm of one hand, and can turn the lever arm 194 in either direction by the thumb of the same hand. Typically, prior art adjustable trocar assemblies require two hands for operation to change.

It is anticipated that the trocar assembly 120 could be modified to accept a ball 162 having more than the two bores 164 and 166 therethrough. For example, the ball 162 might be provided having three bores therethrough. Such a ball 162 could be rotated to a corresponding one of three operating positions by moving the lever arm 194 through a 120 degree arc (60 degrees between a first operating position and a second operating position, and 60 degrees between the second and a third operating position). It is further anticipated that a ball 162 may be provided which would be rotatable to a position in the ball housing 160 which would seal off the opening 158 of the cap 156 to prevent escape of pressure gas through the trocar assembly 120 when no surgical instrument is positioned therein. In such an embodiment, the flap seal 138 may be removed, and, suitably, may be eliminated.

Although the trocar assembly 120 was illustrated and described as having a separate housing 122 and a connectable sleeve 124, it is anticipated that the housing 122 and the sleeve 124 can be formed as a single, inseparable structure.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A trocar assembly comprising:
    a housing having an opening formed therethrough and adapted to receive a surgical instrument therein, said housing defining a distal portion;
    a sleeve defining a proximal portion removably fastened to said distal portion of said housing, said sleeve having a bore aligned with said opening in said housing, which bore is adapted to receive the surgical instrument;
    a split seal positioned within said housing, said split seal having a slit extending therethrough, said split seal effective to maintain a seal through said opening of said housing when a surgical instrument is not inserted through said opening of said housing; and
    a seal assembly positioned within said housing, said seal assembly having a plurality of sealing structures effective to maintain a seal between said housing and surgical instruments of differing diameters which may be inserted through said opening of said housing.

2. The trocar assembly defined in claim 1, wherein said seal assembly includes first and second seals, the combination of said first and second seals effective to maintain a seal between said housing and a surgical instrument inserted through said opening of said housing, said first seal being adapted to maintain a seal between a surgical instrument of a first diameter and said housing, said second seal being adapted to maintain a seal between a surgical instrument of a second diameter and said housing, wherein the first and second diameters are different.

3. The trocar assembly defined in claim 2, wherein said first and second seals are positioned within said housing such that a surgical instrument which is inserted through said opening of said housing is inserted through both said first and second seals.

4. A trocar assembly comprising:
   a housing having an opening formed therethrough and adapted to receive a surgical instrument therein, said opening formed through said housing defines an axis through said housing;
   a split seal positioned within said housing, said split seal having a slit extending therethrough, said split seal effective to maintain a seal through said opening of said housing when a surgical instrument is not inserted through said opening of said housing; and
   a seal assembly positioned within said housing, said seal assembly having a plurality of sealing structures effective to maintain a seal between said housing and surgical instruments of differing diameters which may be inserted through said opening of said housing, said seal assembly including:
      a ball rotatable mounted within said housing and movable to first and second operating positions, said ball defining first and second bores extending through said ball, said first bore being in axial alignment with said opening of said housing when said ball is in said first operating position, said second bore being in axial alignment with said opening of said housing when said ball is in said second operating position;
      a first seal positioned within said first bore of said ball and adapted to maintain a seal between said housing and a surgical instrument having a first diameter which is inserted through said first bore of said ball; and
      a second seal positioned within said second bore of said ball and adapted to maintain a seat between said housing and a surgical instrument having a second diameter, different fiom said first diameter, which is inserted through said second bore of said ball.

5. The trocar assembly defined in claim 1, wherein said housing includes a flange extending radially outwardly therefrom, said sleeve having radially inwardly extending finger portions formed thereon which engage said flange of said housing to fasten said housing to said sleeve.

6. The trocar assembly defined in claim 5, wherein said flange of said housing has radially inwardly extending flats formed therein, said housing being removably fastened to said sleeve by rotationally aligning said flats with said finger portions to disengage said finger portions with said flange.

7. The trocar assembly defined in claim 1, wherein said sleeve includes a tubular wall defining said bore, said tubular wall having a pair of opposed slots formed therethrough.

8. The trocar assembly defined in claim 1, wherein said sleeve has a plurality of stems extending radially outwardly from said sleeve, said plurality of stems being adapted to retain an end of a suture.

9. A trocar assembly comprising:
   a housing having an opening formed therethrough and adapted to receive a selected surgical instrument therein; and first and second seals positioned within said housing, the combination of said first and second seals effective to maintain a seal between said housing and a surgical instrument inserted through said opening of said housing, said first seal being adapted to maintain a seal between said housing and a surgical instrument having a first diameter, said second seal being adapted to maintain a seal between said housing and a surgical instrument having a second diameter, wherein the first and second diameters are different.

10. The trocar assembly defined in claim 9, wherein said first and second seals are positioned within said housing such that a surgical instrument which is inserted through said trocar assembly is inserted through both said first and second seals.

11. The trocar assembly defined in claim 9, wherein said second seal has a slit partially extending therethrough thereby defining first and second lips formed in said second seal.

12. The trocar assembly defined in claim 11, wherein said second seal has a radially inwardly extending circumferential annular bead, said bead having a different sized opening than said first seal, said first seal being adapted to maintain a seal between said housing and a surgical instrument of a first diameter inserted through said first seal, said bead of said second seal being adapted to maintain a seal between said housing and a surgical instrument of a second diameter inserted through said second seal, wherein the first and second diameters are different.

13. The trocar assembly defined in claim 9, wherein said second seal has a proximal end and a distal end, said second seal comprising:
   a flange extending radially outwardly from said proximal end of said second seal;
   a distal portion located at said distal end of said second seal;
   an intermediate portion positioned between said flange and said distal portion; and
   a circumferential bead extending radially inwardly from said intermediate portion, said second seal having a slit formed through said intermediate portion and said distal portion, thereby defining first and second lips.

14. The trocar assembly defined in claim 13, wherein a circumferential groove is formed on the outer surface of said second seal between said intermediate portion and said distal portion, said groove being adjacent said bead.

15. The trocar assembly defined in claim 9, wherein said opening formed through said housing defines an axis through said housing, said trocar assembly further including a sleeve fastened to said housing, said sleeve having a bore formed therethrough in axial alignment with said opening of said housing.

16. The trocar assembly defined in claim 9, wherein said sleeve is removably fastened to said housing.

17. The trocar assembly defined in claim 15 further including a third seal positioned between said sleeve and said housing, said third seal providing sealing between said housing and said sleeve when said housing is fastened to said sleeve.

18. A trocar assembly comprising:
   a housing having an opening formed therethrough, said opening defining an axis through said housing;
   a ball rotatably mounted within said housing and movable to first and second operating positions, said ball having first and second bores extending through said ball, said first bore being in axial alignment with said opening of said housing when said ball is in said first operating position, said second bore being in axial alignment with said opening of said housing when said ball is in said second operating position;

a first seal positioned within said first bore of said ball and adapted to maintain a seal between said housing and a surgical instrument having a first diameter which is inserted through said first bore of said ball and said first seal; and a second seal positioned within said second bore of said ball and adapted to maintain a seal between said housing and a surgical instrument having a second diameter, different from said first diameter, which is inserted through said second bore of said ball and said second seal.

19. The trocar assembly defined in claim 18 further including a seal engaging the outer surface of said ball to maintain a seal between said ball and said housing.

20. The trocar assembly defined in claim 18, wherein said first bore extends through said ball at an angle of about 90 degrees from said second bore.

21. The trocar assembly defined in claim 18 further including a flap seal having a slit defined through a central portion thereof to form first and second flaps, said flaps being distally and inwardly extending and adapted to be urged together by pressurized gas in a distal portion of said trocar assembly.

22. The trocar assembly defined in claim 18, wherein said opening formed through said housing defines an axis through said housing, said trocar assembly further including a sleeve fastened to said housing, said sleeve having a bore formed therethrough in axial alignment with said opening of said housing.

23. The trocar assembly defined in claim 22, wherein said sleeve is removably fastened to said housing.

24. A trocar assembly comprising:

a housing having an opening formed therethrough and adapted to receive a surgical instrument therein;

a sleeve fastened to said housing, said sleeve having a bore aligned with said opening in said housing, which bore is adapted to receive the surgical instrument, said sleeve having a plurality of stems extending radially outwardly from said sleeve said plurality of stems being adapted to retain an end of a suture, a split seal positioned within said housing, said split seal having a slit extending therethrough, said split seal effective to maintain a seal through said opening of said housing when a surgical instrument is not inserted through said opening of said housing; and a seal assembly positioned within said housing, said seal assembly having a plurality of sealing structures effective to maintain a seal between said housing and surgical instruments of differing diameters which may be inserted through said opening of said housing.

* * * * *

UNITED STATES PATENT AND TRADEMARK OFFICE
CERTIFICATE OF CORRECTION

PATENT NO. : 5,993,471
DATED : November 30, 1999
INVENTOR(S) : Riza, et al.

It is certified that error appears in the above-identified patent and that said Letters Patent is hereby corrected as shown below:

Column 11, Claim 4, line 17, change "rotatable" to -- rotatably --.

Column 11, Claim 4, line 31, change "seat" to -- seal --.

Signed and Sealed this

Twentieth Day of June, 2000

Attest:

Q. TODD DICKINSON

*Attesting Officer*     *Director of Patents and Trademarks*